(12) United States Patent
Grinberg et al.

(10) Patent No.: US 7,147,642 B2
(45) Date of Patent: Dec. 12, 2006

(54) ENDPLATE SHAPING DEVICE

(75) Inventors: Alexander Grinberg, Newton, MA (US); Mark Boomer, Bristol, RI (US)

(73) Assignee: Depuy Acromed, Inc., Raynham, MA (US)

( * ) Notice: Subject to any disclaimer, the term of this patent is extended or adjusted under 35 U.S.C. 154(b) by 365 days.

(21) Appl. No.: 10/464,907

(22) Filed: Jun. 19, 2003

(65) Prior Publication Data

US 2004/0002712 A1 Jan. 1, 2004

Related U.S. Application Data

(60) Provisional application No. 60/391,628, filed on Jun. 26, 2002.

(51) Int. Cl.
*A61B 17/00* (2006.01)
(52) U.S. Cl. ........................................ 606/79
(58) Field of Classification Search ................ 606/79, 606/80, 84, 85; 623/17.11–17.16
See application file for complete search history.

(56) References Cited

U.S. PATENT DOCUMENTS

| 5,246,458 | A | 9/1993 | Graham |
| 5,356,414 | A | 10/1994 | Cohen et al. |
| 5,387,215 | A | 2/1995 | Fisher |
| 5,484,446 | A | 1/1996 | Burke et al. |
| 5,486,180 | A | 1/1996 | Dietz et al. |
| 5,688,281 | A | 11/1997 | Cripe et al. |
| 5,910,143 | A | 6/1999 | Cripe et al. |
| 6,030,401 | A | 2/2000 | Marino |
| 6,083,228 | A | 7/2000 | Michelson |
| 6,159,214 | A | 12/2000 | Michelson |
| 6,332,887 | B1 | 12/2001 | Knox |
| 6,755,839 | B1 * | 6/2004 | Van Hoeck et al. .......... 606/87 |
| 6,926,737 | B1 * | 8/2005 | Jackson ................... 623/17.16 |
| 2001/0000532 | A1 | 4/2001 | Michelson |
| 2002/0013588 | A1 | 1/2002 | Larsen |
| 2002/0049444 | A1 | 4/2002 | Knox |
| 2002/0058944 | A1 | 5/2002 | Michelson |
| 2002/0091392 | A1 | 7/2002 | Michelson |
| 2003/0135217 | A1 * | 7/2003 | Buttermann et al. .......... 606/79 |

FOREIGN PATENT DOCUMENTS

| WO | WO 9817208 | 4/1998 |
| WO | WO 9963891 | 12/1999 |

OTHER PUBLICATIONS

DePuy AcroMed, Inc., Pending U.S. Appl. No. 10/101,104.

* cited by examiner

*Primary Examiner*—Eduardo C. Robert
*Assistant Examiner*—Michael J. Araj

(57) ABSTRACT

An improved milling block for use in shaping endplates of opposing vertebral bodies, the block having upper and lower vertical slots for anchoring pins that allow free movement of the adjacent vertebral bodies and a laterally-moving vibratory cutting element.

31 Claims, 15 Drawing Sheets

ENDPLATE SHAPING DEVICE

This application claims priority from now abandoned U.S. Provisional Patent Application No. 60/391,628, filed Jun. 26, 2002, entitled "Endplate Shaping Device".

BACKGROUND OF THE INVENTION

The leading cause of lower back pain arises from rupture or degeneration of lumbar intervertebral discs. Pain in the lower extremities is caused by the compression of spinal nerve roots by a bulging disc, while lower back pain is caused by collapse of the disc and by the adverse effects of bearing weight through a damaged, unstable vertebral joint. One conventional method of managing these problems is to remove the problematic disc and replace it with a prosthetic implant (such as a fusion body, spacer or a motion disk) within the intervertebral disc space.

U.S. Pat. No. 6,083,228 ("Michelson '228") discloses abrading elements particularly designed for preparing the intervertebral space in the spine for reception of the implant between adjacent vertebral bodies. In one embodiment, Michelson '228 discloses a device that includes a handle, a shaft, and a mounting member at one end of the shaft. An abrading element is mounted on the mounting member and is coupled to a drive mechanism. The drive mechanism is operable to move the abrading element in at least one degree of freedom to create surfaces having predetermined contours in the endplates of the adjacent vertebral bodies. FIGS. 21–23 of Michelson '228 disclose vibratory abraders. However, Michelson '228 discloses that the abrader of FIG. 21 produces vibratory motion in a plane generally parallel to the abrading surface of the abrading element. There is no disclosure in Michelson '228 of a vibratory abrader that moves essentially laterally to the instrument shaft.

U.S. Pat. No. 5,387,215 ("Fisher") is a surgical device capable of cutting and removing medium to hard body tissue such as cartilage and bone from a joint region or similarly restricted interior space within the body. The surgical instrument includes a stationary carrier sized for insertion into a joint or similar restricted interior space within the body and having a first and second end. The carrier is provided with an apical aperture at the end to be inserted into the joint. A cutter is axially disposed within the carrier and is provided with at least one cutting surface at one end that protrudes from the aperture of the carrier. The cutter is driven by the motor that moves the cutter in a linearly reciprocating fashion that abrades away tissue depending on the configuration of the cutting surface.

U.S. Pat. No. 6,159,214 ("Michelson '214") discloses a vertebral body milling device for creating a space of selected shape and dimensions across the disk space between adjacent vertebral bodies of the spine, each of the adjacent vertebral bodies having a vertebral endplate adjacent to the disc space, comprising:
i) a milling block configured at least in part for placement across the disc space and against the outer surface of the adjacent vertebral bodies and configured to hold the adjacent vertebral bodies, and comprising:
   a) a front face for placement against the vertebral bodies,
   b) an opposite back face, wherein the milling block has an access aperture configured for providing access for the width of the space to be prepared to at least one of the adjacent vertebral bodies from said back face and through said front face of said milling block, and ii) a bone removal device for removing at least a portion of bone from at least one of the vertebral endplates adjacent the disc space, said bone removal device being configured to access the vertebral endplates through the access aperture.

FIG. 15c of Michelson '214 discloses a milling block in which pin holes are formed through the front and back faces and receive anchoring pins 128 that fixedly secure the milling block to the outer surface of the vertebral bodies. The diameter of the pin hole appears to be essentially equal to that of the pin shank, so that the milling block can not move relative to the vertebral body once anchored by the anchoring pins. The relatively fixed position of the milling block vis-a-vis the vertebrae prevents the opposing vertebrae from moving vertically during insertion of instruments such as distractors or rotary drills. Accordingly, the front lips of the vertebrae are necessarily removed during endplate preparation. These lips may be important in retaining the implant within the disc space.

FIG. 19 of Michelson '214 discloses a milling block in which a bone removal device passes through the block via an entry opening 114 in the block that is wider than it is tall. The predominant width of the aperture allows the bone removal device to move transverse to its longitudinal axis so that wide portions of the vertebral endplates adjacent the disc space are milled by a relatively small diameter milling tool to create a rectangular-shaped space for receiving the implant. However, since the cutting element is moved transversely over a significant distance (i.e., at least twice the diameter of the cutting element), the prepared disc space has a substantially uniform height across that transverse axis, and not a curved height that more closely mimics the natural contours of the disc space.

Therefore, it is an object of the present invention to provide a milling block that helps the surgeon to retain the endplate lips.

It is another object of the present invention to provide a milling block that provides helps the surgeon provide a contoured disc space height across the transverse axis.

SUMMARY OF THE INVENTION

The present inventors have found that providing vertically disposed slots on the milling block allows the vertebrae to move freely vertically on either side of the milling block. Therefore, when a cutting element disposed distal to the milling block is inserted into the disc space, the vertical freedom provided to the vertebrae allows the disc space to open and easily accept the cutting element. Since the vertebrae are not fixed by the milling block, but are free, the cutting element need not horizontally plow through the front lips of the endplate in order to enter the disc space. Accordingly, the endplate lips (which are important to implant retention) are preserved.

Therefore, in accordance with the present invention, there is provided a milling block for use in a vertebral body milling device for creating a contoured disc space between adjacent vertebral bodies of a spine, the milling block comprising:
   a) a front face for placement against the adjacent vertebral bodies,
   b) a first slot formed in a direction substantially perpendicular to the front face and having a vertical length, and
   c) a first anchoring pin received in the first slot, and having a proximal portion having a diameter, wherein the vertical length of the first slot is greater than the diameter of the proximal portion of the first anchoring pin.

In addition, the present inventors have recognized that there is no requirement that the cutting element must access the disc space only by passing through the back opening of the milling block, as in Michelson '214. Rather, the cutting tool can be preassembled so that the cutting element is disposed substantially distal to the front face of the milling block. Since the cutting element no longer need fit within the back opening of the milling block, the cutting element may have a width exceeding that of the back opening. This discovery that the cutting element may be wider than the entry opening allows for the production of a contoured disk space having a more substantially contoured height in the transverse direction.

Therefore, in accordance with the present invention, there is provided a vertebral body milling device for creating a contoured disc space between adjacent vertebral bodies of the spine, each of the adjacent vertebral bodies having a vertebral endplate adjacent to the disc space, comprising:
i) a milling block comprising:
   a) a front face for placement against the vertebral bodies,
   b) an opposite back face having a back opening having a width, and
   c) a housing formed between the front and back faces, and
ii) a bone removal device for contouring vertebral endplates, comprising:
   a) a distal cutting element having a width and disposed distal the front face of the milling block,
   b) an intermediate element housed within the housing, and
   c) a proximal longitudinal element having a distal portion disposed in the back opening, wherein the width of the distal cutting element is greater than the width of the back opening.

Since a relatively wide cutting element is now possible, there is no need to provide a back opening that is wider than it is tall in order to increase the width of the prepared disc space. Therefore, in some embodiments, the bone removal device of the present invention can be received in a milling block having a back opening that substantially conforms to the longitudinal element of the bone removal device. The conformation between these components increases the precision of the milling operation. Therefore, in accordance with the present invention, there is provided a vertebral body milling device for creating a contoured disc space between adjacent vertebral bodies of the spine, each of the adjacent vertebral bodies having a vertebral endplate adjacent to the disc space, comprising:
i) a milling block comprising:
   a) a front face for placement against the vertebral bodies,
   b) an opposite back face having a back opening, and
   c) a housing formed between the front and back faces, and
ii) a bone removal device for contouring vertebral endplates and comprising:
   a) a distal cutting element disposed distal the front face of the milling block,
   b) an intermediate element housed within the housing, and
   c) a proximal longitudinal element having a distal portion disposed in the back opening, wherein the back opening of the milling block substantially conforms to the distal portion of the longitudinal element of the bone removal device.

DETAILED DESCRIPTION OF THE INVENTION

Figure 1:
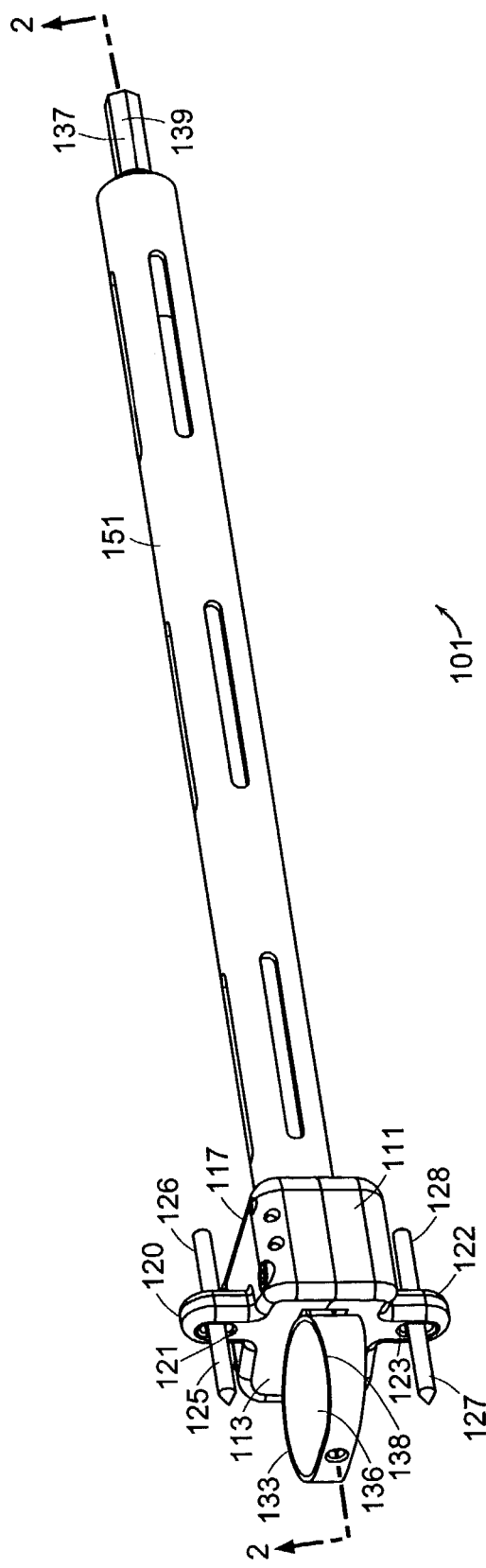
FIG. 1 discloses a perspective view of an assembled version of a vertebral body milling device of the present invention.
Figure 2:
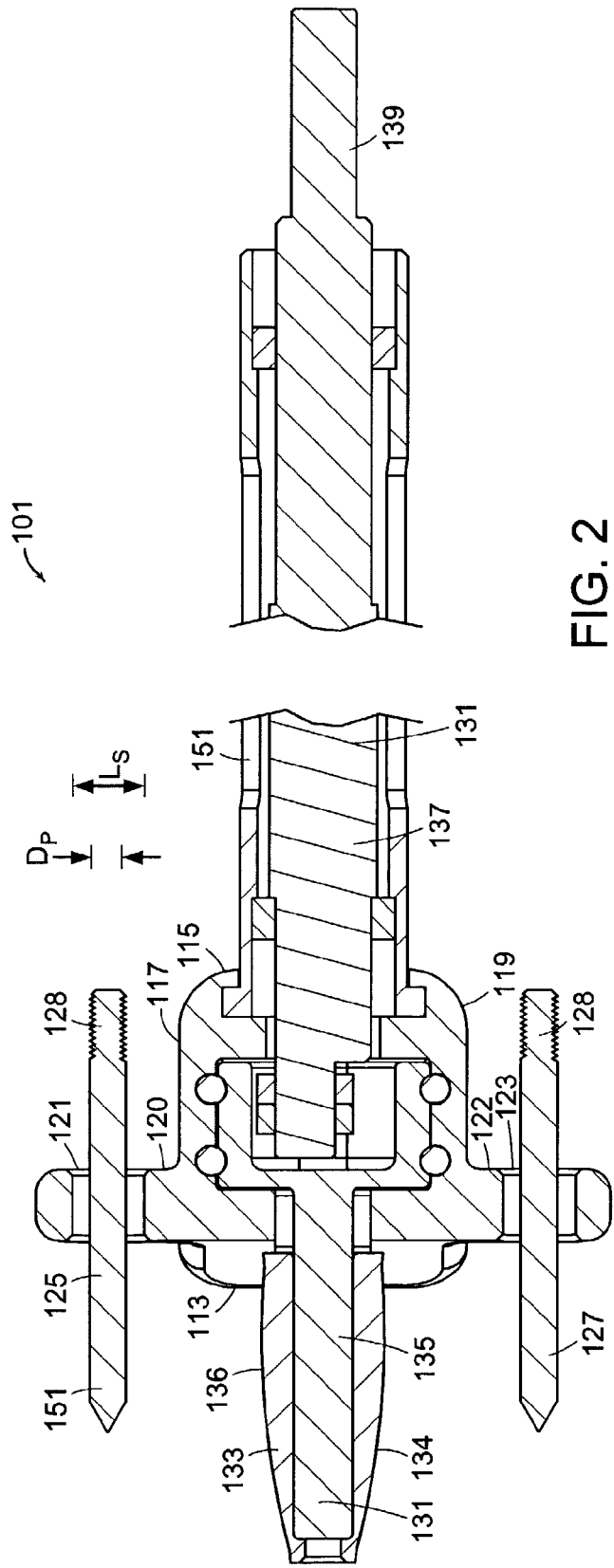
FIG. 2 discloses a cross-sectional side view of a vertebral body milling device of the present invention.

Now referring to FIGS. 1 and 2, there is provided a vertebral body milling device 101 for creating a contoured disc space, each of the adjacent vertebral bodies having a vertebral endplate adjacent to the disc space, comprising:
i) a milling block 111 configured at least in part for placement across the disc space and against the outer surfaces of the adjacent vertebral bodies, comprising:
   a) a front face 113 for placement against the vertebral bodies,
   b) an opposite back face 115,
   c) upper 117 and lower 119 faces connecting the front and back faces, and
   d) first 120 and second 122 tabs extending from the respective upper and lower faces and having first 121 and second 123 slots formed therein, each slot formed in a direction substantially perpendicular to the front face and having a vertical length and a diameter, e) first 125 and second 127 anchoring pins received in the respective first and second slots, each pin having a proximal portion having a diameter, and ii) a bone removal device 131 for removing bone from vertebral endplates, comprising:

a) a distal cutting element 133, b) an intermediate vibratory element 135, and c) a proximal longitudinal element 137 having a distal portion configured to access the vibratory element and defining a longitudinal axis, wherein the intermediate vibratory element 135 is housed within the milling block, the distal cutting element is disposed substantially distal to the front face of the milling block, and the distal portion of the proximal longitudinal element is received in the vibratory element.

In use, anchoring pins 125,127 are first inserted into the outer surfaces of opposing vertebral bodies (not shown) at a preliminarily-defined midline. Second, a distracting instrument (not shown) grasps the pins and moves them in opposite directions so that the opposing vertebral bodies become distracted. The distraction of the vertebrae will allow for the future insertion into the disc space of a cutting element 133 without requiring the removal of the front lips of the vertebral endplate.

Third, the slots 121,123 of the milling block are aligned with the anchoring pins, and the milling block is pushed over the proximal portion 126,128 of the anchoring pins so that the proximal portion of the anchoring pins are received in the slots and the cutting element 133 is received into the disc space. The depth of insertion of the cutting element is limited by the front face 113 of the milling block.

Therefore, in accordance with the present invention, there is provided a method of creating a contoured disc space between adjacent vertebral bodies of a spine, each of the adjacent vertebral bodies having a vertebral endplate adjacent to the disc space and an anterior lip, comprising the steps of:

a) inserting a first anchoring pin having a proximal diameter into a first of the adjacent vertebral bodies, b) providing a vertebral body milling device having a first vertical slot disposed thereon and a distally disposed cutting element, the vertical slot having a length being greater than the proximal diameter of the first anchoring pin, c) receiving the first slot over the first anchoring pin, d) inserting the cutting element into the disc space so that the first pin vertically moves within the first slot and the disc space opens to accept the cutting element and preserve the lips.

Alternatively, the milling block can first be inserted into the disc space, and then the pins can be inserted into the opposing vertebral bodies by passing through the slots provided on the milling block.

Therefore, in accordance with the present invention, there is provided method of creating a contoured disc space between adjacent vertebral bodies of the spine, each of the adjacent vertebral bodies having a vertebral endplate adjacent to the disc space and an anterior lip, comprising the steps of:

a) placing upon the adjacent bodies a vertebral body milling device having a first vertical slot disposed thereon and a distally disposed cutting element, b) inserting a first anchoring pin having a diameter into a first of the adjacent vertebral bodies through the first vertical slot, the first vertical slot length being greater than the pin diameter, c) inserting the cutting element into the disc space so that pin vertically moves within the slot and the disc space opens to accept the cutting element and preserve the lips.

Fourth, as the surgeon holds the device by sheath 151, a drive mechanism, such as an electrical drill (not shown), is then attached to the proximal end 139 of the longitudinal element 137.

Fifth, the drive mechanism is activated, thereby causing the longitudinal element to rotate. The rotational motion of the longitudinal element is converted by the vibration element 135 into lateral vibrating motion in the cutting element 133, thereby causing the cutting surfaces 134,136 of the cutting element to shape the opposing endplates. The freedom provided by slots 121,123 allows vertebral body movement in a direction substantially normal to the cutting surfaces 134,136 of the cutting element, while keeping the bodies aligned with each other. Moreover, as the cutting element shapes the opposing vertebral endplates, the tension provided by the disc's annulus and adjacent muscular structures upon the cutting element provides supporting axial forces that keep the opposing endplates biased against the cutting element. Accordingly, by vibrating the cutting element 133, both endplates of the vertebral bodies can be shaped simultaneously.

Sixth, when the depth of cut (i.e., the penetration of a cutting surface into the surface of the endplate) proceeds to the point where the uncut periphery of the endplate surface contacts the non-cutting ledge 138 that surrounds the periphery of the cutting element, the cutting surface is prevented from further penetrating the endplate. When this occurs, the surgeon stops the drive mechanism, and the device is removed.

Figure 6:
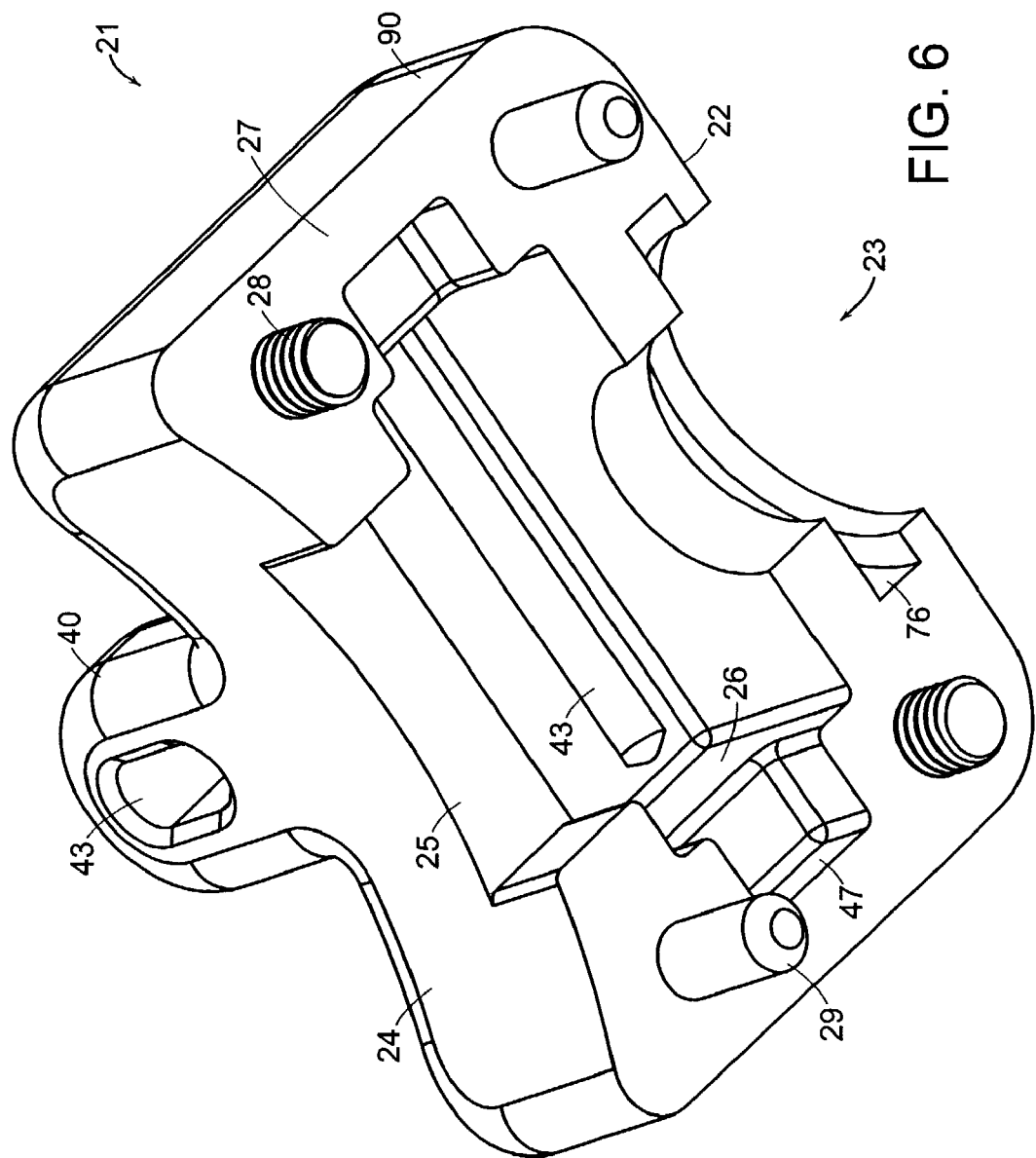
FIG. 6 discloses a perspective view of the upper shell portion of a milling block component of a vertebral body milling device of the present invention.
Figure 7:
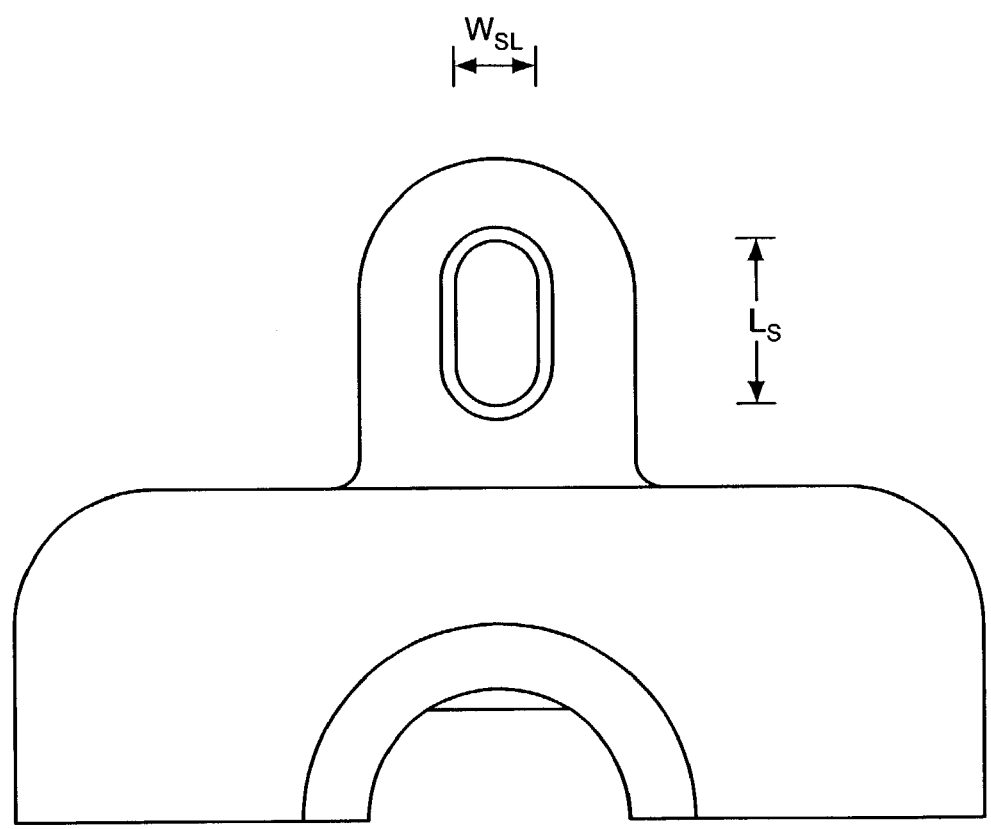
FIG. 7 discloses a distal view of the upper shell portion of a milling block component of a vertebral body milling device of the present invention.
Figure 8:
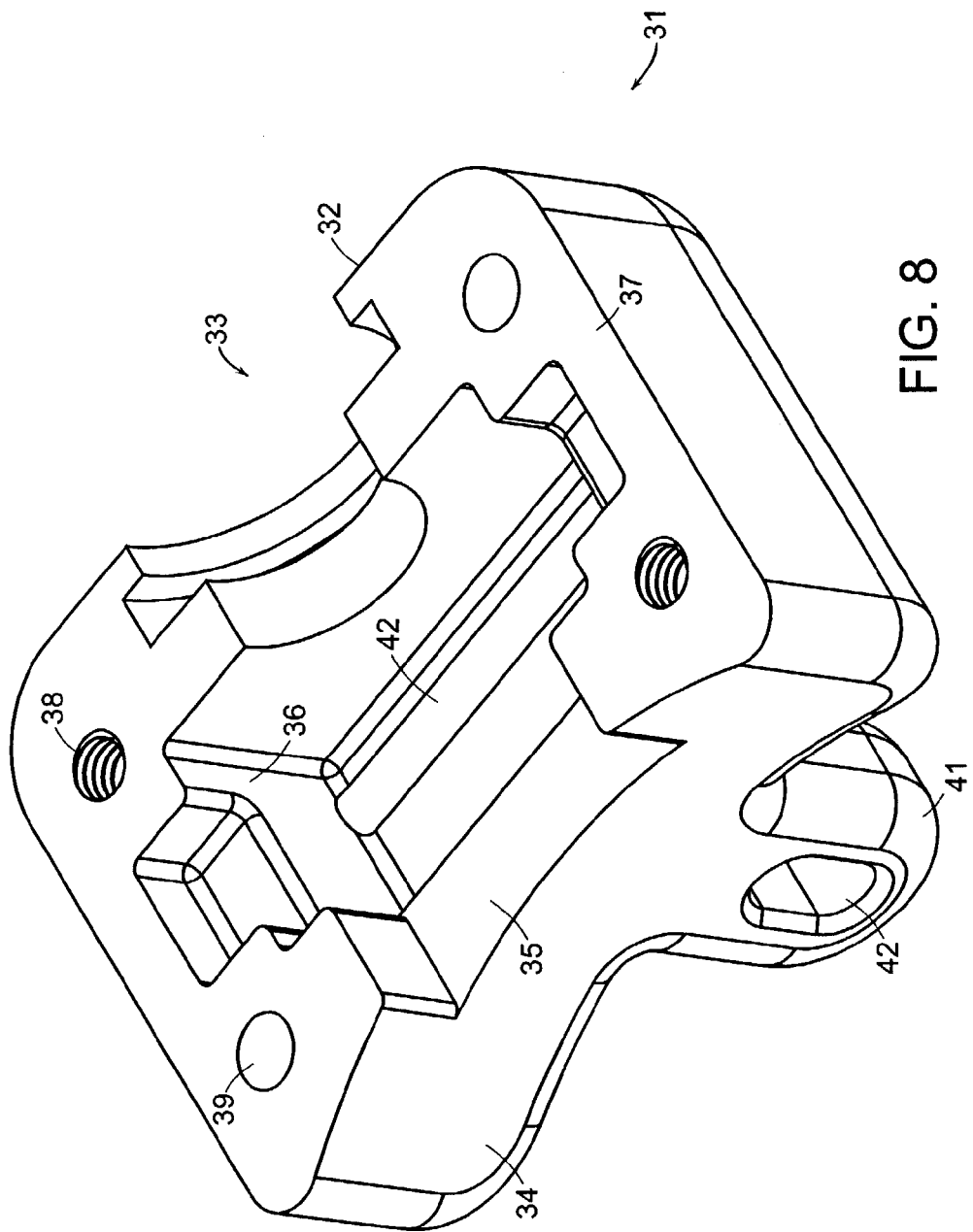
FIG. 8 discloses a perspective view of the lower shell portion of a milling block component of a vertebral body milling device of the present invention.

Now referring to FIGS. 6–8, in preferred embodiments, the milling block 111 comprises a first shell 21 and a second shell 31. Preferably, each shell comprises a back half-face 22,32 having a half-opening 23,33 formed therein, a front half-face 24,34 having a half-opening 25,35 formed therein, and an inner recess 26,36 communicating with each front and back half-opening. Each shell also has matching inside attachment surfaces 27,37.

The shells may fit together in an upper-lower arrangement or a side-side arrangement. Preferably, however, the shells are designed to fit together in an upper-lower arrangement, as this arrangement allows tabs and slots to be conveniently placed upon each shell in alignment with the respective upper and lower vertebrae. In the case of FIGS. 6 and 8, first shell 21 is preferably the upper shell and second shell 31 is preferably the lower shell.

Figure 3:
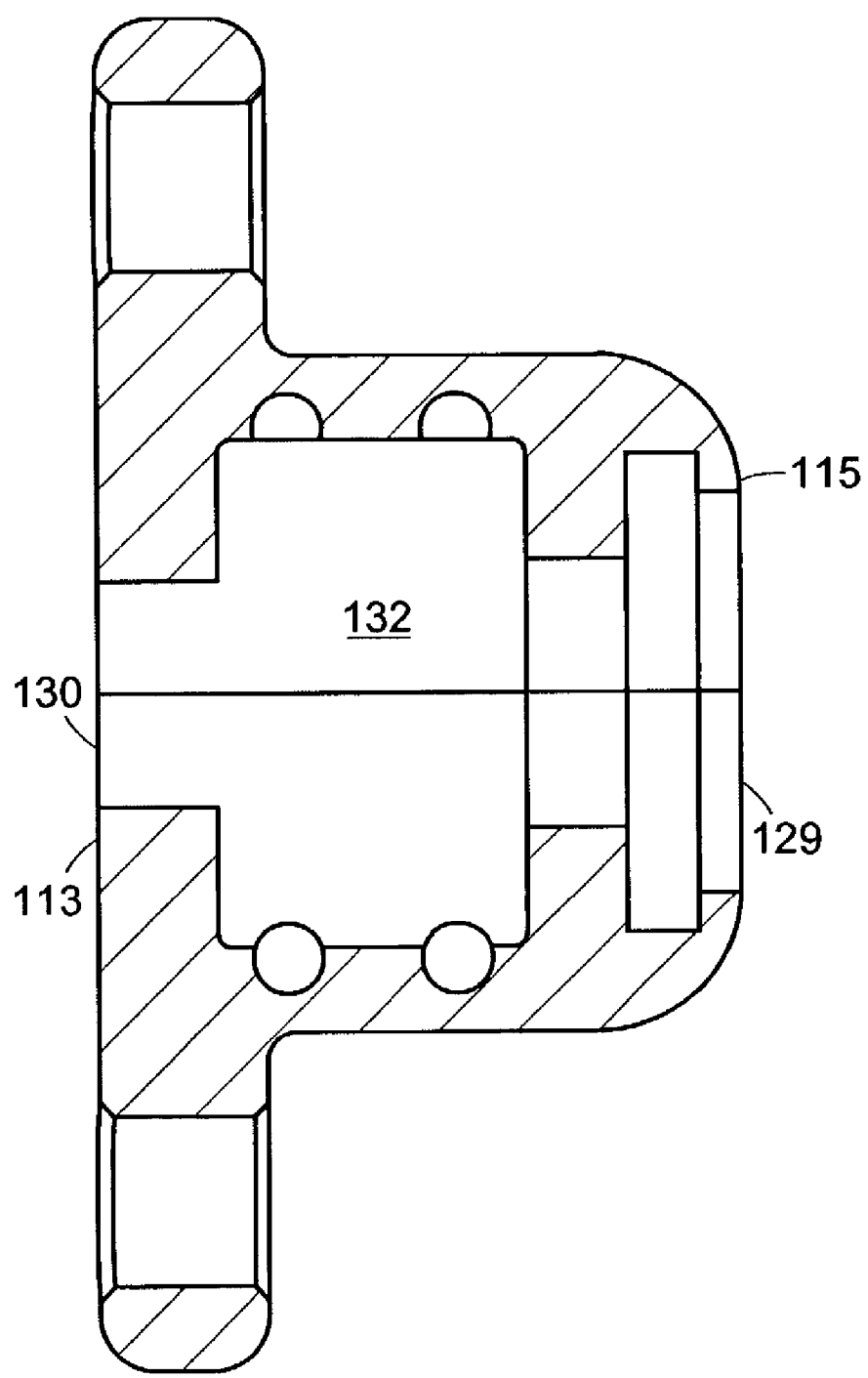
FIG. 3 discloses a cross-sectional view of aligned half-shells forming a milling block of the present invention.

Now referring to FIG. 3 as well, when the shells are assembled, the two inside attachment surfaces 27, 37 are aligned and fit together and form the milling block 111. Once assembled, front half-faces 24, 34 form the front face 113, while back half-faces 22,32 form back face 115. Preferably, the front face of the milling block is shaped so as to conform to the shape of the outer surfaces of the adjacent vertebral bodies. Since the outer surfaces of the vertebral bodies are typically convex in nature, the face of the milling block is preferably of a concave shape.

In preferred embodiments, when the two inside attachment surfaces are aligned and fit together, the opposing recesses and half-openings form a continuous space comprising a back opening 129 formed in the back face 115 of the milling block, a front opening 130 formed in the front face of the milling block, and a housing 132 formed within the milling block for receiving the vibration element and connecting the respective front and back openings.

Therefore, in accordance with the present invention, there is provided a vertebral body milling device for creating a contoured disc space between adjacent vertebral bodies of the spine, each of the adjacent vertebral bodies having a vertebral endplate adjacent to the disc space, comprising:

i) a milling block comprising:
   a) an upper shell having a front half-face, a back half-face, and an inside attachment surface connecting the half-faces,
   b) a lower shell having a front half-face, a back half-face, and an inside attachment surface connecting the half-faces, wherein the inside attachment surface of the upper shell is substantially aligned with the inside attachment surface of the lower shell.

In some embodiments, the alignment of the inside attachment surfaces aligns the front half-faces to form a front face in the milling block. Preferably, the alignment of the inside attachment surfaces aligns the back half-faces to form a back face in the milling block. Preferably, the upper shell further comprises a front half-opening formed in the front half-face, the lower shell further comprises a front half-opening formed in the front half-face, and the substantial alignment of the inside attachment surfaces aligns the front half-openings to form a front opening in the milling block. Preferably, the upper shell further comprises a back half-opening formed in the back half-face, the lower shell further comprises a back half-opening formed in the back half-face, and the substantial alignment of the inside attachment surfaces aligns the back half-openings to form a back opening in the milling block. Preferably, the upper shell further comprises an intermediate recess, the lower shell further comprises an intermediate recess, and the substantial alignment of the inside attachment surfaces aligns the intermediate recess to form a housing in the milling block.

Again referring to FIGS. 6–8, in this embodiment, the first and second shells further comprise attachment means (in this case, a screw 28 and a matching threaded hole 38) for fastening the two shells together. In one instance, the hole of the attachment means extends completely through the first shell and ends blindly within the second shell. Thus, the device can be easily disassembled by simply removing two screws (28 of FIG. 6) that attach the upper and lower shells. This allows each piece to be easily resterilized and therefore reusable.

The first and second shells in this embodiment further comprise alignment means (in this case, a dowel 29 and a matching blind hole 39) for easily aligning the two shells prior to their attachment. In one instance, the hole of the alignment means begins on the inside attachment surface of the second shell and ends blindly therewithin, while the dowel extends from the inside attachment surface of the first shell.

Now referring to FIG. 3, in some embodiments, the assembly of the half-shells leaves a gap between inside attachment surfaces of the shells. This gap, which is typically on the order of 0.1–0.2 mm, desirably allows the assembly to accommodate the movement of the vibrating element.

Now referring to FIGS. 6–8, the milling block also comprises tabs 40,41 extending from the upper and lower faces, wherein the tabs have slots 42,43 formed therein in a direction substantially perpendicular to the respective front half-faces. The slots are designed to receive at least the proximal portion of the anchoring pins and thereby provide alignment of the vertebral bodies at the midline and prevent undesirable lateral movement of the vertebral bodies during milling.

Figure 5:
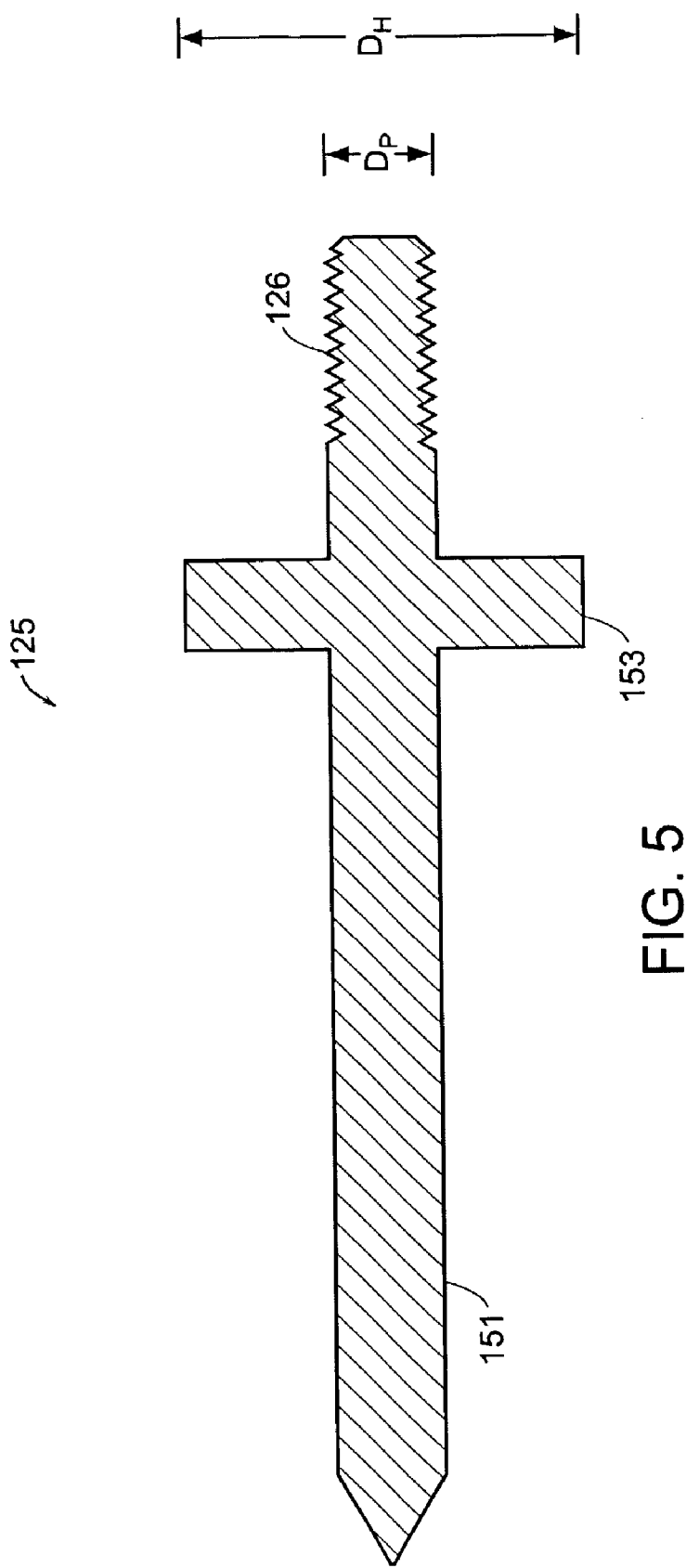
FIG. 5 discloses a cross-sectional view of an anchoring pin of the present invention.

Now referring to FIGS. 5 and 7, preferably, the slots have a vertical length $L_S$ that is longer than the diameter $D_P$ of the proximal portion of the anchoring pins. When this condition is met, the anchoring pin may move freely vertically within the slot and so the vertebral bodies are free to move vertically in either direction and thereby easily accept insertion of the cutting element. Because the cutting element is easily accepted during insertion, the endplate lips are not removed during either insertion or cutting.

In the device of FIG. 1, the tabs forming the slots extend from the upper and lower faces of the milling block. However, in other embodiments of the invention, the tabs can extend from the side face (e.g., side face 90 in FIG. 6) of the milling block. In other embodiments of the invention, the slots can be formed through the front and back faces of the milling block.

In the device of FIG. 1, the slots are closed. However, in other embodiments, the slot may be an open slot formed between two parallel projections extending from a face, wherein the end portions of the projections do not touch. Such an open slot will still provide the alignment function. However, a closed slot is preferred because it limits the device to a predetermined range of vertical freedom.

Now referring to FIGS. 1, 5 and 7, anchoring pins 125, 127 are received in the slots 121,123 and limit the lateral migration of the milling block. Prevention of lateral migration is particularly important in devices having laterally vibrating cutters. In preferred embodiments, the anchoring pin 125 comprises a distal shank 151 shaped so as to be inserted and received in the outer surface of the vertebral body, a head portion 153 having a diameter $D_H$ that is greater than the width $W_{SL}$ of the slot in order to act as a stop against excessive penetration of the pin into the vertebral body, and a proximal portion 126 having a diameter $D_P$ less than the diameter $D_{SL}$ of the slot so that it may be received in and move freely in vertical slot of the milling block. If desired, a cap may be provided on the proximal end of the pin after reception in the slot to prevent expulsion.

Therefore, in accordance with the present invention, there is provided a milling block for use in a vertebral body milling device for creating a contoured disc space between adjacent vertebral bodies of the spine, each of the adjacent vertebral bodies having a vertebral endplate adjacent to the disc space, the milling block comprising:
   a) a front face for placement against the adjacent vertebral bodies,
   b) a first slot formed in a direction substantially perpendicular to the front face and having a diameter, and
   c) a first anchoring pin received in the first slot, and having a proximal portion having a diameter, wherein the diameter of the first slot is greater than the diameter of the proximal portion of the first anchoring pin.

The freedom of movement provided by the anchoring pin and the slot of the present invention allow the surgeon to insert the anchoring pin into the vertebral body, distract the vertebral body (thereby opening the disc space), and then fit the milling block over the distracted pins, thereby advantageously allowing the opened disc space to easily accept the cutting element without harming the endplate lips.

In other embodiments, the anchoring pin has no head portion so that its width along its entire longitudinal dimension is smaller than the slot width. In such embodiments, the surgeon can insert the pin into the slot after the cutting element has been inserted into the disc space. In such cases, the surgeon can provide proper alignment of the assembly by using x-ray technology to align the milling block.

Now referring to FIG. 2, in preferred embodiments, the bone removal device 131 comprises a distal cutting element 133, a vibration element 135 and a proximal longitudinal element 137. The modular nature of the bone removal device 131 allows different sized cutting elements to be selected at the point of care, based on the different sizes of the implants to be implanted.

The cutting element of the present invention is disposed at the distal end of the bone removal device and can be any element suitable for cutting bone, including but not limited to, vibrating cutting elements, burrs, router bits, abraders, grinders, rasps, drills, graters saws, oscillating cutters, reciprocating cutters, orbital cutters, and lasers.

Preferably, the cutting element is a vibratory cutting element. More preferably, it is a laterally-vibrating cutting element. In some embodiments, the cutting element has a shape which corresponds substantially to the shape of the artificial disc to be implanted.

Figure 11:
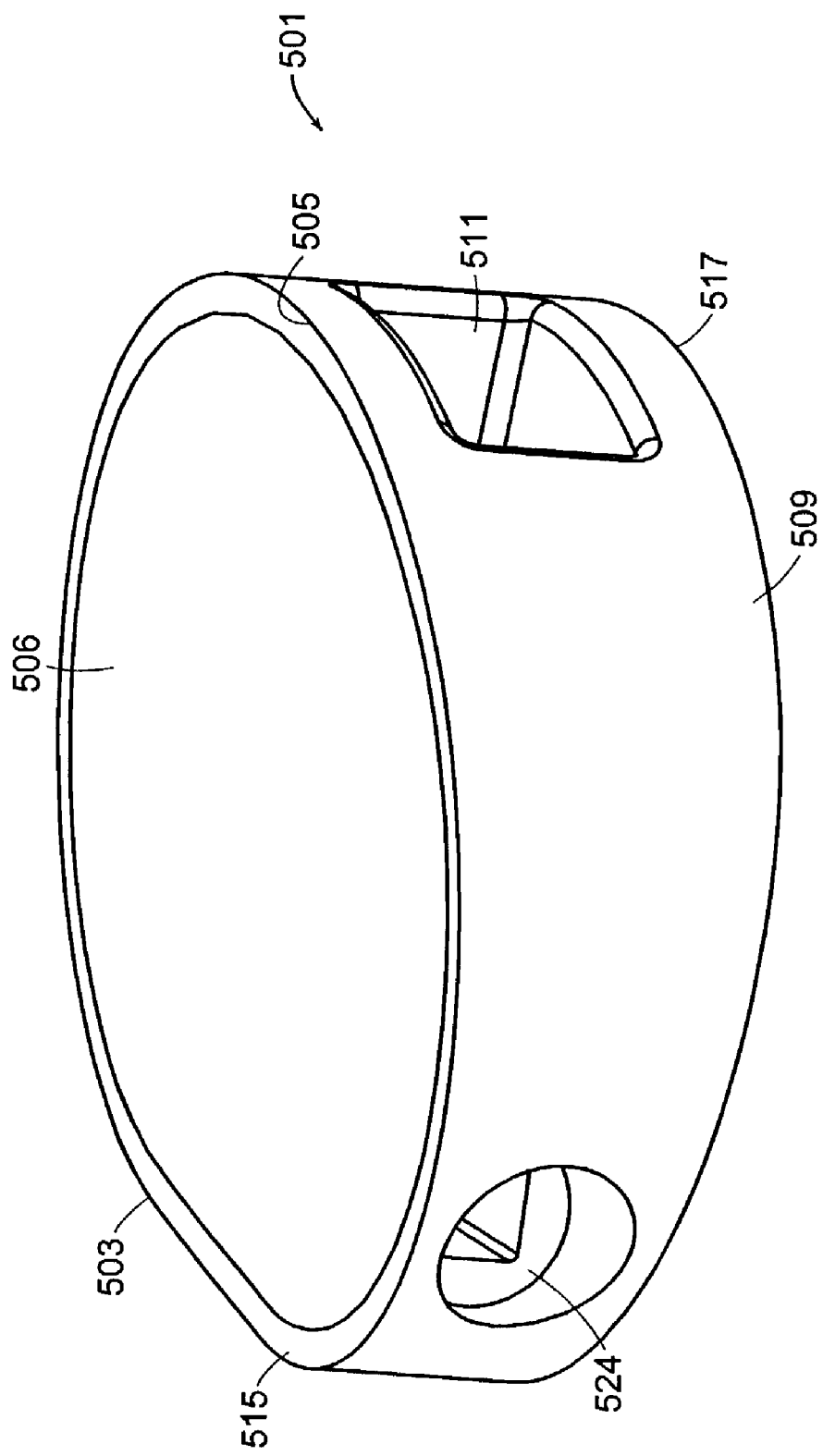
FIG. 11 discloses a perspective view of the cutting element component of a vertebral body milling device of the present invention.

Now referring to FIG. 11, preferably, cutting element 501 comprises a distal end portion 503, a proximal end portion 505, upper cutting surface 506, and lower cutting surface (134 of FIG. 2), and a peripheral sidewall 509 therebetween.

A cutting surface of the cutting element may reside on either one or two endplate-facing sides of the cutting element. Preferably, the cutting surface resides on both the upper and lower sides of the cutting element. Preferably, both cutting surfaces of the cutting element are shaped to substantially correspond to the contour of the implant and comprise cutting teeth (not shown). These teeth may also be produced by chemical etching.

In some embodiments, the peripheral sidewall of the cutting element forms a non-cutting ledge 515 disposed between the opposing cutting faces. As a device having such a feature is pressed vertically into an endplate, the inner portion of the endplate is first contoured by the contour of the cutting surfaces at an ever-increasing depth. However, once a certain depth has been reached, the non-cutting ledge contacts an uncut peripheral portion of the endplate, and thereby prevents further cutting into the endplate. Accordingly, the non-cutting nature of this ledge provides a convenient stop for the vertical penetration of the device and so desirably limits the depth of cut by a cutting face into an opposing endplate. In some embodiments, the peripheral sidewall forms upper 515 and lower 517 non-cutting ledges. In some embodiments, the sidewall comprises an upper non-cutting peripheral ledge facing the upper cutting surface and a lower non-cutting peripheral ledge facing the lower cutting surface.

Therefore, in accordance with the present invention, there is provided a cutting element for contouring a vertebral endplates adjacent a disc space, comprising:

i) upper and lower surfaces, and
ii) a peripheral sidewall formed between the upper and lower surfaces, wherein at least one of the upper and lower surface comprises a cutting surface, and wherein the sidewall comprises a non-cutting peripheral ledge.

The height of the cutting element is designed to be at least as great as the disc space to be contoured, and is generally has a height which is identical to or slightly smaller than (within 1–2 mm) the implant height.

Figure 9:
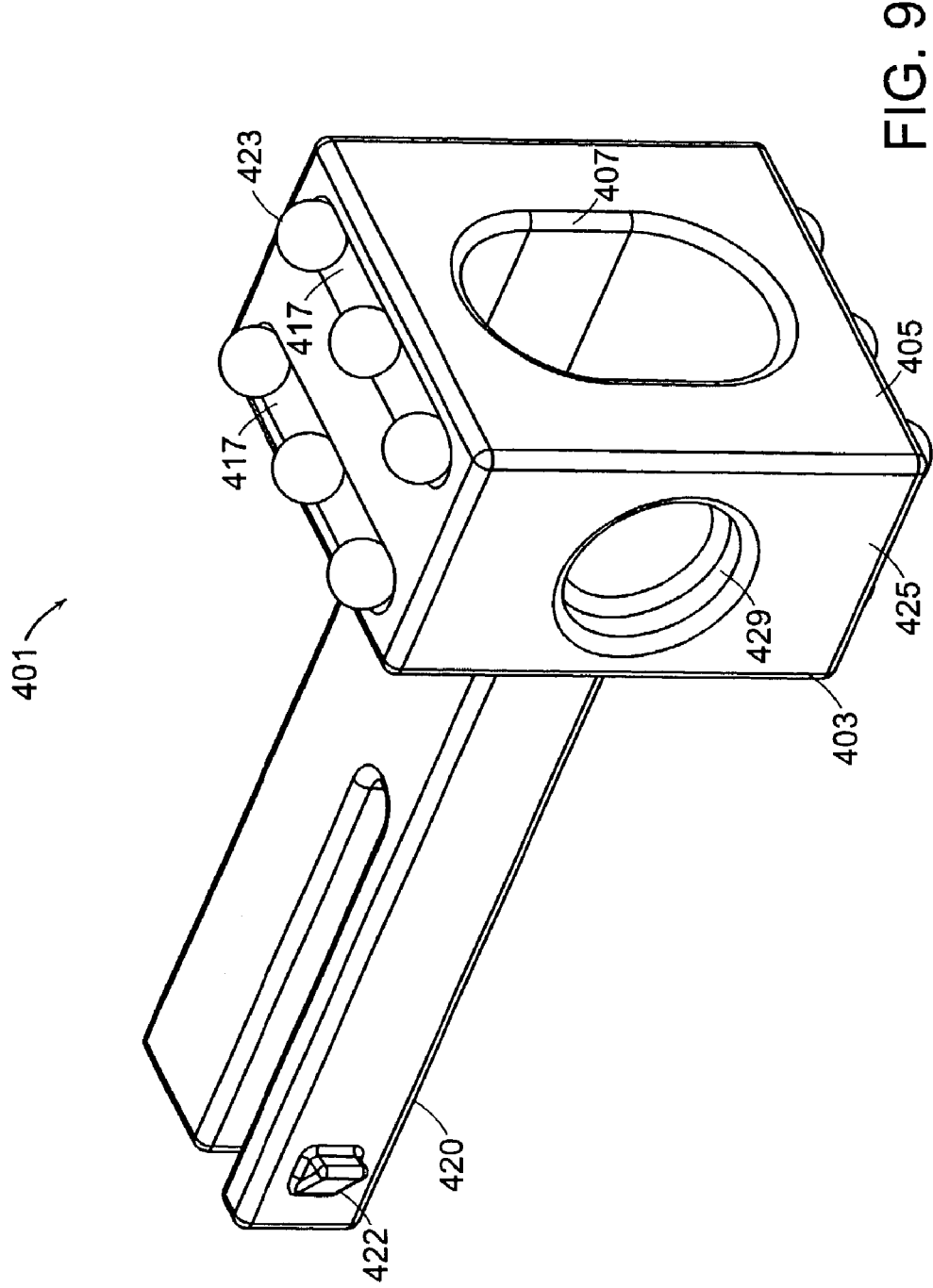
FIG. 9 discloses a perspective view of a vibration element component of a vertebral body milling device of the present invention.

The proximal portion of the cutting element preferably comprises an attachment means 511 (in this case, a slot disposed in the peripheral sidewall) for attaching to the remainder of the bone removal device. The slot 511 allows for a quick disconnect of the shaft 420 of the vibration element (as shown in FIG. 9) by allowing flexion of the shaft wall. The proximal portion of the cutting element further comprises a hole 524 extending into the cutting element to communicate with slot 511. The communicating portion of this hole 524 is designed to mate with and retain the tooth 422 of the vibration element (as shown in FIG. 9). To disconnect the cutting element 133 from the vibration element, a simple square or round pin can be inserted into hole 524 and pushed against the tooth 422 to disengage the tooth from the hole.

In some embodiments, the intervertebral body implant itself can be used as a cutting element for shaping the endplates, preferably using either lateral or circular vibration.

Now referring to FIG. 9, in preferred embodiments, vibration element 401 is housed substantially within the housing created by mating of the first and second shells to form the milling block. The vibration element comprises a distal face 403 and a proximal face 405. The distal face comprises an attachment means 420 (in this case, a square shaft) for attachment to the cutting element. Typically, the attachment means extends through the front opening of the milling block. Proximal face 405 comprises a recess 407 that receives the distal end portion of the longitudinal element.

The function of the recess 407 is to convert the rotational motion of the longitudinal element in vibratory motion. Now referring to FIG. 10 as well, preferably, the recess has a substantially rectangular shape (in this case, ovoid) formed by upper 409 and lower 411 inner walls, and lateral inner sidewalls 413, 415. Now referring also to FIG. 10, preferably, the distance $D_{U-L}$ between the upper and lower walls is at least as great as the diameter of the distal portion of the longitudinal element. In this condition, the vibration element does not move vertically in response to rotation of the longitudinal element. Similarly, the distance $D_L$ between the lateral sidewalls is greater than the diameter $D_E$ of the eccentric projection, but is less than the diameter $D_{SW}$ of the circle formed by the sweep of the eccentric projection by rotation of the longitudinal element. In this condition, the vibration element moves laterally in response to rotation of the longitudinal element.

The stroke of the vibration is preferably in the range of from 1 mm to 5 mm, and is more preferably within the range of from 1 mm to 2 mm. When the stroke is in the preferred range, the cutting element can produce a substantial contour in the endplate suitable for holding an implant, but still substantially retain the shape of the cutting element. The frequency of vibration can vary depending on the size of the cutting element and other factors, and is generally between 100 and 100,000 vibrations per minute, and is preferably between 2000 and 10,000 vibrations per minute.

Again referring to FIGS. 9 and 10, in preferred embodiments, the vibrating element 401 further comprises two radiused grooves 417 formed in opposing outer faces of the vibration element. In one embodiments, the grooves are disposed on the upper 419 and lower 421 faces of the vibration element. Further, a plurality of bearing balls 423 are disposed in the grooves. The balls may be retained by a retainer (not shown) for ease of assembly and sterilization. The grooves in the vibrating element are designed to mate with similar grooves 42,43 disposed in the lower and upper shells of FIGS. 6–8.

Typically, components received within a milling block are capable only of sliding motion. However, sliding motion typically produces a great deal of wear particles and debris.

In contrast, rolling contact typically produces much less wear. The present inventors are unaware of a component housed within a vertebral milling block that is designed for rolling contact motion with the milling block. Therefore, in accordance with the present invention, there is provided a vertebral body milling device for creating a contoured disc space between adjacent vertebral bodies of a spine, comprising:

i) a milling block comprising:
  a) a front face for placement against the vertebral bodies and having a front opening,
  b) an opposite back face, and
  c) a housing formed between the front and back faces, and
ii) a bone removal device for contouring vertebral endplates and comprising:
  a) a distal cutting element disposed substantially distal the front face of the milling block, and
  b) a proximal vibration element substantially housed within the housing of the milling block and in connection with the distal cutting element through the front opening of the milling block.

Preferably, the milling block is formed from an upper shell having an inside attachment surface and an upper front half-face, and a lower shell having an inside attachment surface and a lower front half-face, and the inside attachment surface of the upper shell is substantially aligned with the inside attachment surface of the lower shell, and wherein alignment of the inside attachment surfaces aligns the half faces to produce the front face.

Preferably the upper shell further comprises a front half-opening, the lower shell further comprises a front half-opening, and wherein alignment of the inside attachment surfaces aligns the front half-openings to produces the front opening.

Preferably, the upper shell further comprises a back half-opening, the lower shell further comprises a back half-opening, and alignment of the inside attachment surfaces aligns the back half-openings to produces a back opening.

Preferably, the upper shell further comprises an intermediate recess, the lower shell further comprises an intermediate recess, and alignment of the inside attachment surfaces produces aligns the recesses to produce the housing.

The vibration element further comprises outer sidewalls 425, 427. Now referring to FIGS. 4 and 6, in preferred embodiments, first and second compression springs 261,263 are disposed between an outer sidewall of the vibration element and an inner wall 45 (in FIG. 6) of a shell. These springs compress as the vibration element moves to the extreme laterally, and the resistive force of such compression helps stabilize and smooth the motion of the vibration element. Preferably, the outer sidewalls of the vibration element has at least one blind hole 429 (in FIG. 9) formed therein for seating the compression springs. These holes are formed opposite blind holes 47 (in FIG. 6) formed in the inner walls of the two shells.

Figure 10:
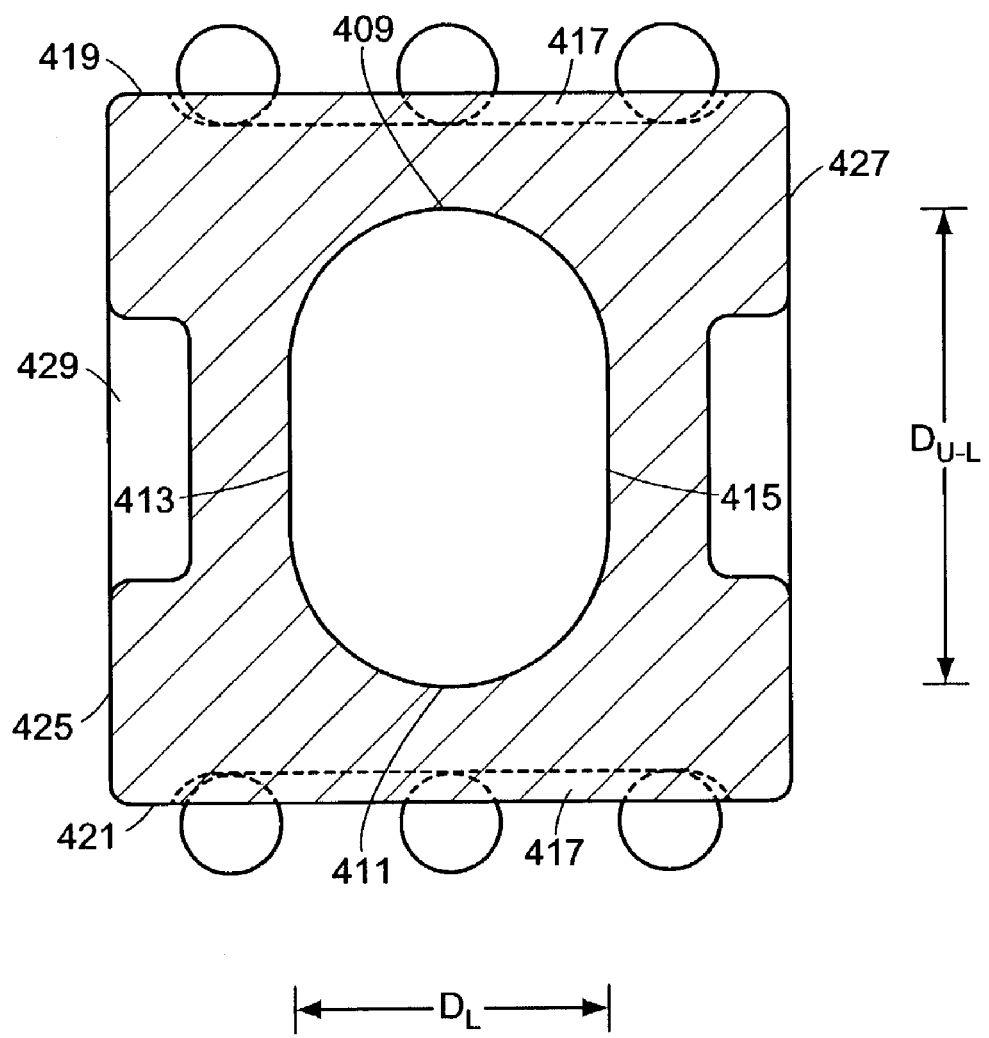
FIG. 10 discloses a distal view of the vibration element component of a vertebral body milling device of the present invention.

In some embodiments, as in FIGS. 9 and 10, the smaller dimension of the recess 407 is disposed in a direction substantially transverse to the longitudinal axis of the device. In this condition, the vibration element produces essentially lateral movement. When the cutting element is disposed distal to the vibration element and is oriented as shown in FIG. 1, it also vibrates in essentially a lateral direction. Essentially lateral vibration of the cutting element makes the device safer since it is not moving in the direction of the spinal canal. The present inventors are not aware of any conventional vibratory device for use in endplate preparation that provides essentially lateral vibratory movement. Preferably, grooves 417 are likewise disposed in the direction transverse to the longitudinal axis of the device.

Therefore, in accordance with the present invention, there is provided a vertebral body milling device for creating a contoured disc space between adjacent vertebral bodies of the spine, each of the adjacent vertebral bodies having a vertebral endplate adjacent to the disc space, comprising:

i) a bone removal device for contouring vertebral endplates, comprising:
  a) a distal cutting element,
  b) an intermediate vibration element comprising a proximal face having a recess having a vertical dimension and a lateral dimension, and
  c) a proximal longitudinal element defining a longitudinal axis, wherein the distal cutting element vibrates in a direction essentially lateral to the longitudinal axis.

Also in accordance with the present invention, there is provided a vibration element for use in a bone removal device for contouring vertebral endplates, comprising:
  a) a proximal face having a recess having a vertical dimension and a lateral dimension,
  b) a distal face having an attachment means for connecting to a cutting element, wherein the lateral dimension of the recess is less than the vertical dimension of the recess.

Also in accordance with the present invention, there is provided a bone removal device for contouring vertebral endplates, comprising:

i) a vibration element comprising:
  a) a proximal face having a recess forming lateral inner side walls, and upper and lower walls,
  b) a distal face having an attachment means for connecting to a cutting element,
ii) a longitudinal element having a distal end having an eccentric projection, wherein the eccentric projection is received in the recess of the vibration element, and wherein rotation of the longitudinal element causes the eccentric projection to contact substantially only the lateral inner sidewalls of the recess.

Figure 13:
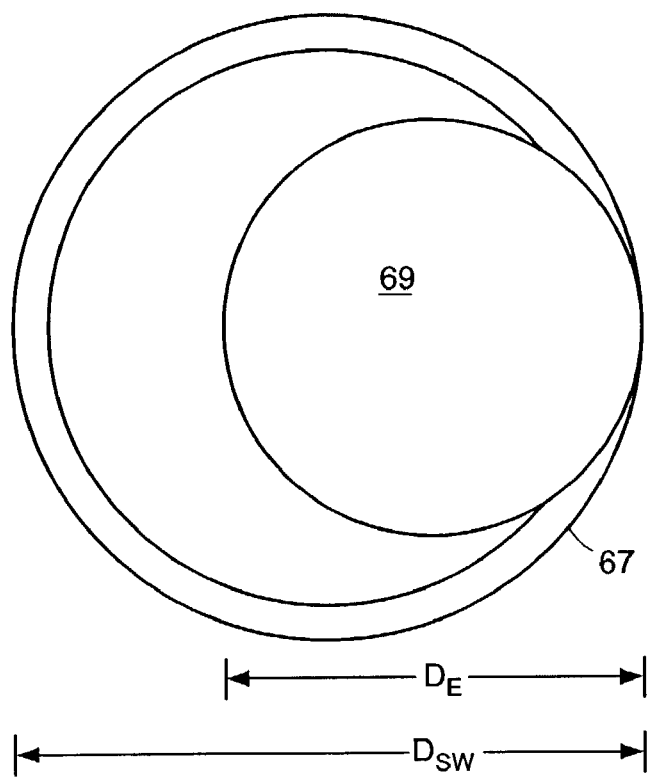
FIG. 13 discloses a distal view of the longitudinal element component of a vertebral body milling device of the present invention.

Now referring to FIGS. 10 and 13, the lateral movement (or "stroke") of the vibration element is the diameter $D_{SW}$ of the sweep produced by rotation of the eccentric projection of the longitudinal element. In preferred embodiments, the stroke is between 1 and 5 mm, more preferably between 1 mm and 2 mm.

Figure 4:
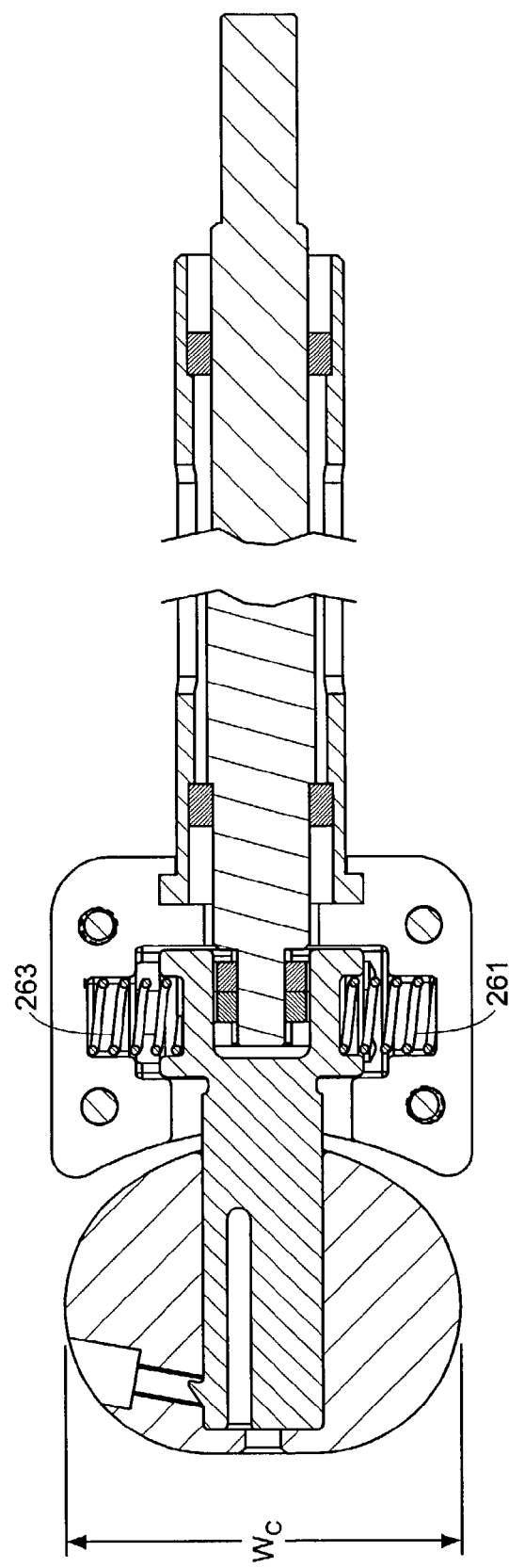
FIG. 4 discloses a cross-sectional top view of a vertebral body milling device of the present invention.

Now referring to FIGS. 4 and 10, in some embodiments, the ratio of the width $W_C$ of the cutting device to the lateral movement of the vibrating element is greater than 1:1, preferably at least 2:1, more preferable at least 5:1, more preferably at least 10:1. As this ratio increases, the contour of the prepared endplate becomes more substantially similar to that of the cutting element. Most preferably, this ratio is in the range of 10:1 to 30:1.

Figure 12:
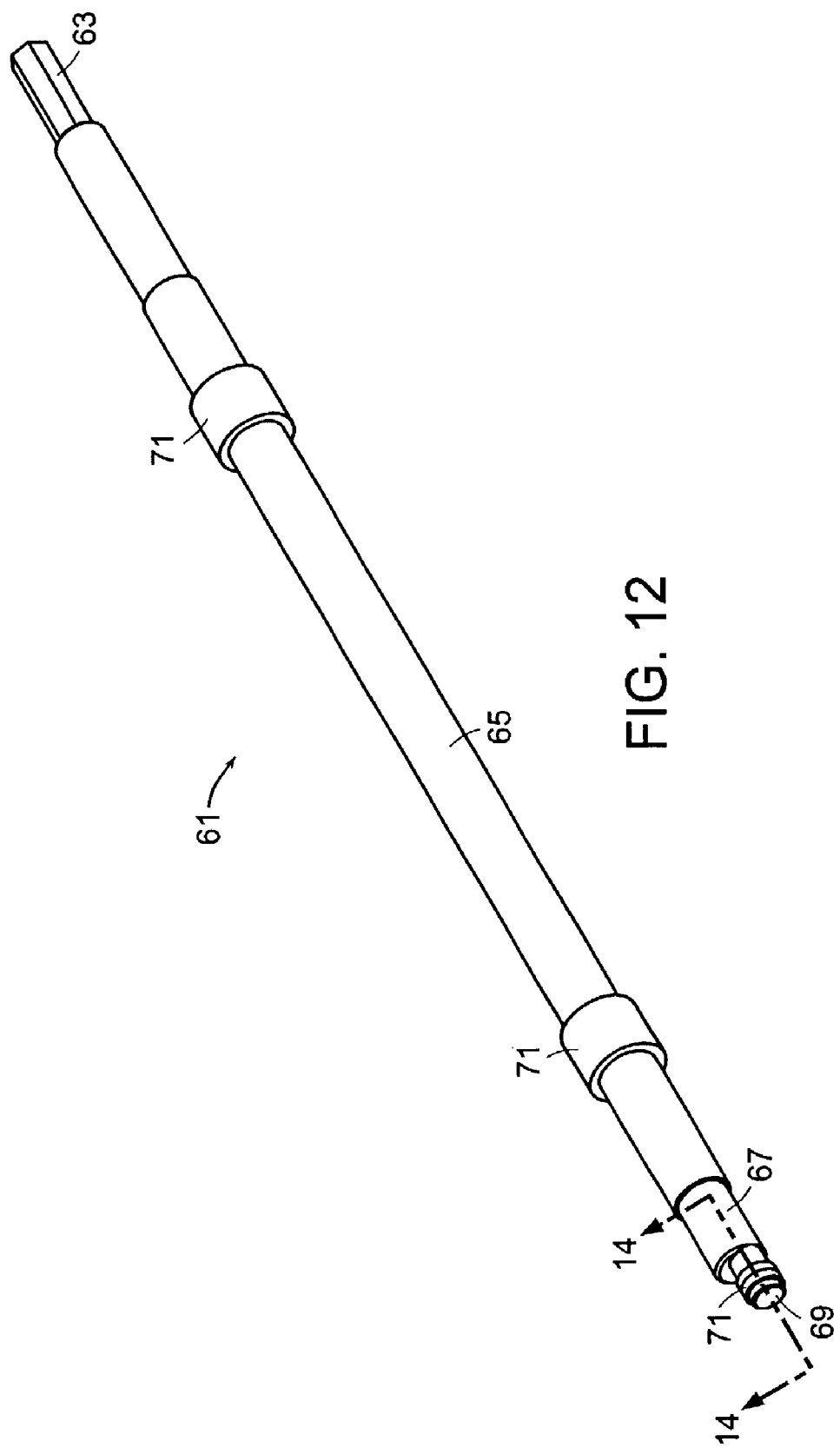
FIG. 12 discloses a perspective view of the longitudinal element component of a vertebral body milling device of the present invention.

Now referring to FIGS. 12 and 13, longitudinal element 61 comprises a proximal end portion 63, an intermediate shank 65, and a distal end 67. The distal end is preferably sized to fit through the back opening of the milling block. Extending from the distal end of the longitudinal element is eccentric projection 69, which is sized to fit within the recess of the vibration element. When the longitudinal element is rotated about its longitudinal axis, the eccentric projection sweeps out a circle having a diameter $D_{SW}$ and contacts in an alternating fashion the lateral sidewalls of the recess of the vibration element, thereby producing lateral movement of the vibration element. The diameter of the shank is designed to fit within sheath 5. Longitudinal element preferably comprises a rod or a tube, but is more preferably a rod.

Figure 14:
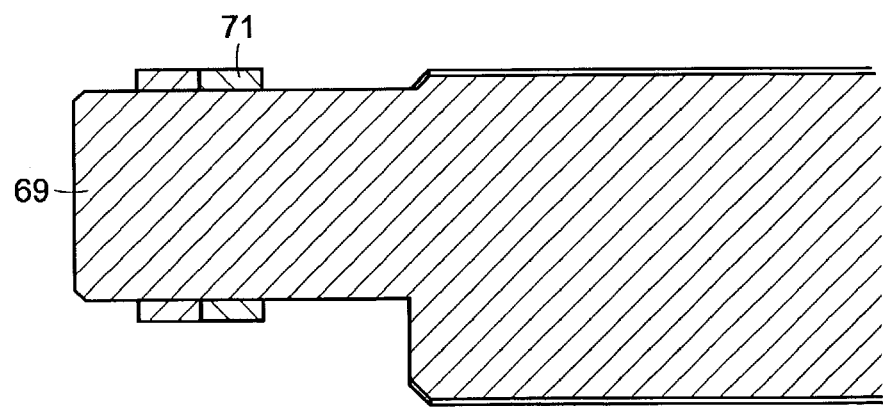
FIG. 14 discloses a cross-sectional view of the distal portion of the longitudinal element having a bearing fitted upon the eccentric projection.

The longitudinal element may further comprise a plurality of ball bearings 71 pressed onto the shank. Now referring to FIG. 14, the distal-most bearing 71 is fitted upon the eccentric projection 69 and is also sized to be inserted into the recess 407 of the vibration element. These bearings reduce friction and particle shedding.

Figure 15:
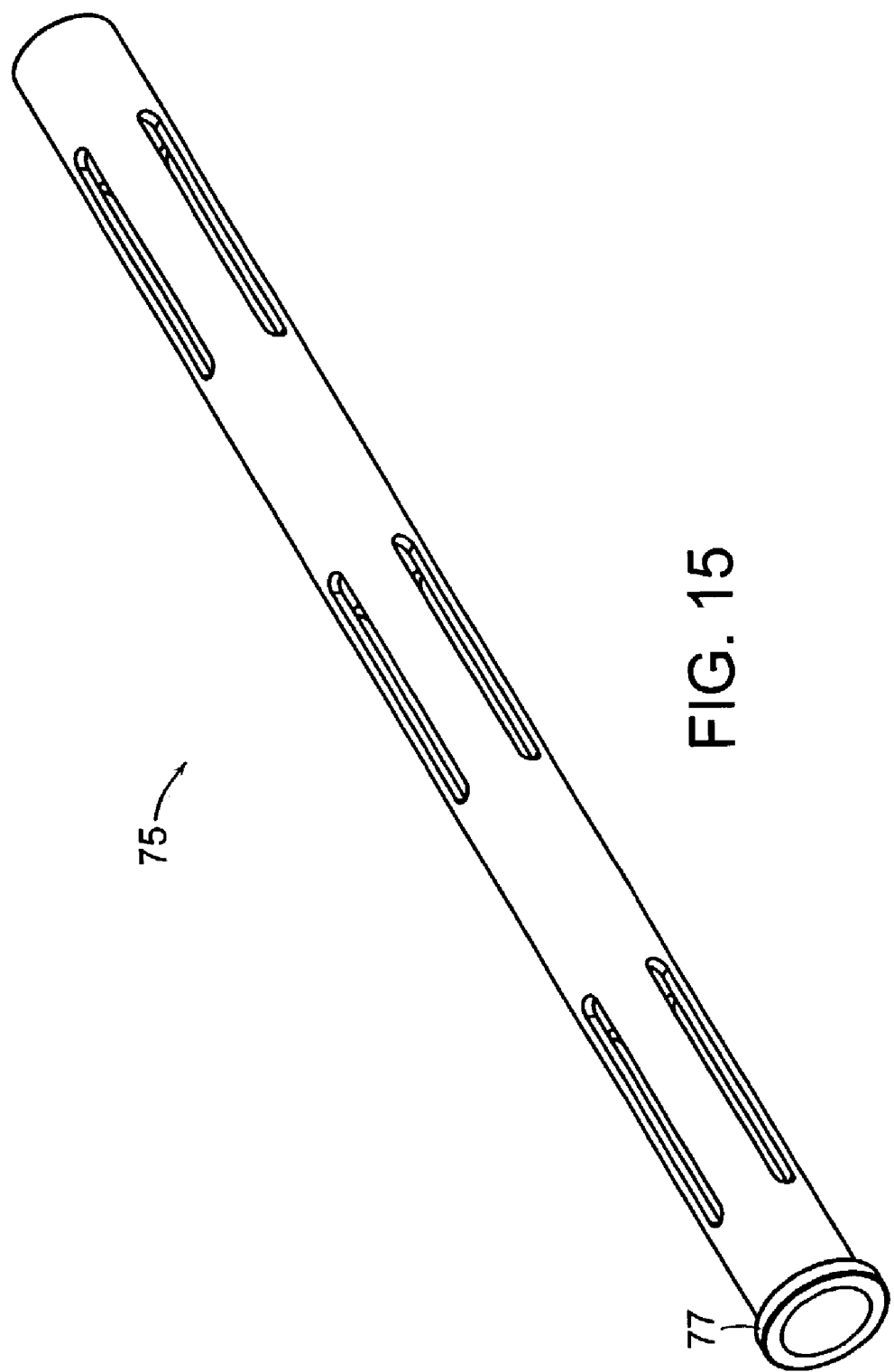
FIG. 15 discloses a perspective view of the sheath component of a vertebral body milling device of the present invention.

Now referring to FIG. 15, sheath 75 is shaped so as to allow gripping by the surgeon for the handle (not shown) or is fixed to a retraction system for better alignment and rigidity. The longitudinal element is easily inserted into the sheath 75 and aligned through the bearings 71 with the sheath.

In some embodiments, sheath 75 is attached to the lower and upper shells by first inserting the flange 77 into a groove (76 in FIG. 6) in the milling block, and then inserting the longitudinal element into the sheath.

Preferably, the longitudinal element and vibration element are shaped so that rotation of the longitudinal element causes a preferred directional movement in the vibration element. More preferably, the distal end of the longitudinal element has an eccentric projection fitted with a bearing that is sized to fit within an rectangular-shaped recess of the vibration element. When the longitudinal element is rotated around its longitudinal axis, the eccentric projection sweeps a circular pattern. In the upper and lower portions of the circle created by the sweep, the projection moves freely within the upper and lower portions of the recess within the vibratory element (and so produces no movement in the vibration element). In the lateral portions of the swept circle, the projection meets the lateral inner sidewalls of the recess and pushes them laterally. This lateral force upon the inner sidewalls produces lateral movement in the vibration element. Bearing balls housed within grooves of the vibration element and contacting the mating grooves of the first and second shells help lower the friction associated with the vibratory movement. The lateral movement of the vibration element transmits a reciprocating transverse force to the proximal end of the cutting element to which it is attached. This reciprocating transverse force causes lateral vibration of the cutting element.

In some embodiments, the device can be driven by attachment of the proximal end of the longitudinal element to a standard hospital electrical drill, and so is convenient to use.

Figure 16:
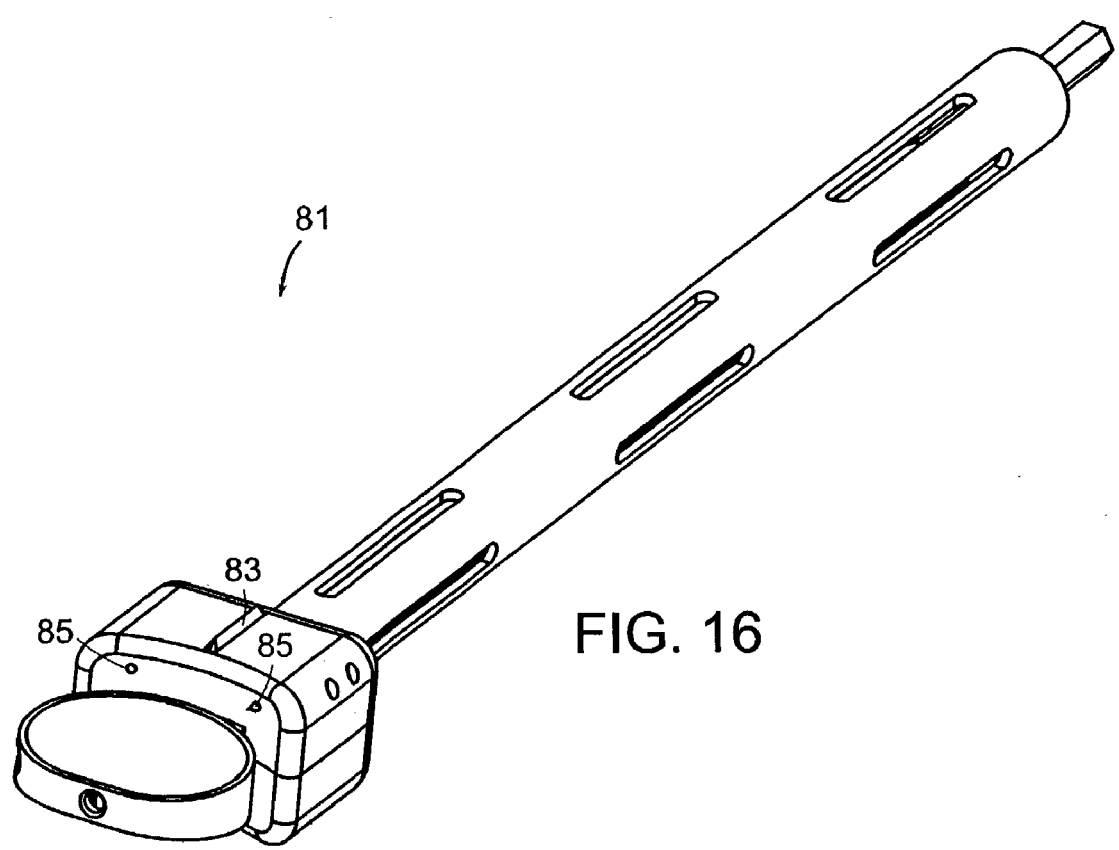
FIG. 16 discloses a perspective view of an assembled version of a second vertebral body milling device of the present invention.

Now referring to FIG. 16, there is provided a second embodiment of the device 81 of the present invention. The device of FIG. 16 differs from that of FIG. 1 in that it does not have the vertical slots for aligning the anchoring pins, but rather has a center pointer 83 disposed along the centerline of the milling block that helps the surgeon align the device to a predetermined midline. Undesired lateral movement of the device is prevented by two small tapered protrusions 85 extending distally from the front face of the milling block that can project into the outer surface of the opposing vertebrae. Since the insertion of these tapered protrusions will also eliminate the desirable feature of freedom of vertical movement of the vertebrae against the cutting tool, a cutting element used with this device may be made in a two piece spring-loaded design that allows each half of the cutting tool to be pressed against opposite endplate during cutting.

Alternatively, the cutting element of this second embodiment may be provided as a solid, one-piece design having a cutting surface only upon the side of the cutting element opposite the side of the tapered protrusion. In use, the cutting element of such a device is inserted and shaping is performed on the single endplate contacting the cutting element. Next, the device is removed, rotated 180 degrees and reinserted to shape the opposite endplate.

Typically, the milling block and cutting tool components of the present invention can be made out of any material commonly used in instruments used in spinal interbody operations, including hardened stainless steel alloys, such as Custom 455 Stainless, available from Carpenter Specialty Alloys of Wyomissing, Pa. The cutting surfaces can be made from metals such as stainless steel or conventional abrasives composites. If the device is designed to be reusable, then it is preferred that all the components be made of stainless steel. If the device is designed to be disposable, then it is preferred that some of the components be made of plastic.

In sum, the device of the present invention provides a simple, safe and compact design that can be driven by a standard hospital electrical drill. Some of the benefits produced by at least some of the selected embodiments of the device of the present invention include, but are not limited to, the following:

distraction of the intervertebral space and ease of insertion of the cutting tool,
 acceptance of the cutting element into the disc space while preserving the endplate lips,
 prevention of excessive cutting depth into the endplates,
 precision contouring of the endplates,
 lateral cutting motion,
 aggressive cutting teeth created by chemical etching technology or conventional milling processes, and
 a simple transmission mechanism providing vibration of the cutting element that is based on the rolling friction, thereby eliminating shedding of the particles that would be produced having sliding friction between the parts.

We claim:

1. A vertebral body milling device for creating a contoured disc space between adjacent vertebral bodies of the spine, each of the adjacent vertebral bodies having a vertebral endplate adjacent to the disc space, comprising:
   i) a milling block comprising:
      a) a front face for placement against the vertebral bodies,
      b) an opposite back face having a back opening having a width, and
      c) a housing formed between the front and back faces, and
   ii) a bone removal device for contouring vertebral endplates, comprising:
      a) a distal cutting element having a width and disposed distal the front face of the milling block,
      b) an intermediate element housed within the housing, and
      c) a proximal longitudinal element having a distal portion disposed in the back opening,
   wherein the width of the distal cutting element is greater than the width of the back opening
   wherein the intermediate element is a vibratory element, and
   wherein the cutting element is a vibratory cutting element comprising teeth formed by chemical etching.

2. The device of claim 1 wherein the vibratory cutting element has a shape corresponding substantially to the shape of an interbody implant.

3. The device of claim 1 wherein the vibratory element produces a stroke of between 1 mm and 3 mm.

4. The device of claim 3 wherein the vibratory cutting element has a width, wherein the ratio of the width to the stroke is at least 1:1.

5. The device of claim 4 wherein the ratio is at least 2:1.

6. The device of claim 4 wherein the ratio is at least 5:1.

7. The device of claim 4 wherein the ratio is between 10:1 and 30:1.

8. A vertebral body milling device for creating a contoured disc space between adjacent vertebral bodies of the spine, each of the adjacent vertebral bodies having a vertebral endplate adjacent to the disc space, comprising:
   i) a milling block comprising:
      a) a front face for placement against the vertebral bodies,
      b) an opposite back face having a back opening, and
      c) a housing formed between the front and back faces, and
   ii) a bone removal device for contouring vertebral endplates and comprising:
      a) a distal cutting element disposed distal the front face of the milling block,
      b) an intermediate element housed within the housing, and
      c) a proximal longitudinal element having a distal portion disposed in the back opening,
wherein the back opening of the milling block substantially conforms to the distal portion of the longitudinal element of the bone removal device, and
wherein the intermediate element is a vibratory element, and wherein the cutting element is a vibratory cutting element comprising teeth formed by chemical etching.

9. The device of claim 8 wherein the vibratory cutting element has a shape corresponding substantially to the shape of an interbody implant.

10. The device of claim 8 wherein the vibratory element produces a stroke of between 1 mm and 3 mm.

11. The device of claim 10 wherein the vibratory cutting element has a width, wherein the ratio of the width to the stroke is at least 1:1.

12. The device of claim 11 wherein the ratio is at least 2:1.

13. The device of claim 11 wherein the ratio is at least 5:1.

14. The device of claim 11 wherein the ratio is between 10:1 and 30:1.

15. A vertebral body milling device for creating a contoured disc space between adjacent vertebral bodies of a spine, comprising:
   i) a milling block comprising:
      a) a front face for placement against the vertebral bodies and having a front opening,
      b) an opposite back face, and
      c) a housing formed between the front and back faces, and
   ii) a bone removal device for contouring vertebral endplates and comprising:
      a) a distal cutting element disposed substantially distal to the front face of the milling block, and
      b) a proximal vibration element substantially housed within the housing of the milling block and in connection with the distal cutting element through the front opening of the milling block,
wherein the milling block is formed from an upper shell having an inside attachment surface and an upper front half-face, and a lower shell having an inside attachment surface and a lower front half-face, and wherein the inside attachment surface of the upper shell is substantially aligned with the inside attachment surface of the lower shell, and wherein alignment of the inside attachment surfaces aligns the half faces to produce the front face,
wherein the upper shell further comprises a front half-opening, the lower shell further comprises a front half-opening, and wherein alignment of the inside attachment surfaces aligns the front half-openings to produces the front opening,
wherein the upper shell further comprises a back half-opening, the lower shell further comprises a back half-opening, and wherein alignment of the inside attachment surfaces aligns the back half-openings to produces a back opening,
wherein the upper shell further comprises an intermediate recess, the lower shell further comprises an intermediate recess, and
wherein alignment of the inside attachment surfaces produces aligns the recesses to produce the housing.

16. The device of claim 15 wherein the inside attachment surfaces of the shells comprise attachment means.

17. The device of claim 15 wherein the inside attachment surfaces of the shells comprise alignment means.

18. The device of claim 15 wherein the alignment of the inside surfaces produces a gap therebetween.

19. The device of claim 15 wherein the back face of the milling block comprises a back opening.

20. The device of claim 15 wherein the bone removal device further comprises:
   c) a longitudinal element having a distal portion disposed within the back opening of the back face of the milling block.

21. A vertebral body milling device for creating a contoured disc space between adjacent vertebral bodies of the spine, each of the adjacent vertebral bodies having a vertebral endplate adjacent to the disc space, comprising:
   i) a bone removal device for contouring vertebral endplates, comprising:
      a) a distal cutting element,
      b) an intermediate vibration element comprising a proximal face having a recess having a vertical dimension and a lateral dimension, and
      c) a proximal longitudinal element defining a longitudinal axis,
wherein the distal cutting element vibrates in a direction essentially lateral to the longitudinal axis, and
wherein the recess forms upper and lower walls having a distance therebetween, and lateral inner sidewalls having a distance therebetween, and the distance between the lateral inner sidewalls is less than the distance between the upper and lower walls.

22. The device of claim 21 wherein the proximal longitudinal element comprises a distal eccentric projection.

23. The device of claim 22 wherein the eccentric projection is received within the recess of the intermediate vibration element.

24. The device of claim 21 wherein the cutting element has a width and the vibration element produces a stroke, and wherein the ratio of the width of the cutting element to the stroke is at least 1:1.

25. A vertebral body milling device for creating a contoured disc space between adjacent vertebral bodies of the spine, each of the adjacent vertebral bodies having a vertebral endplate adjacent to the disc space, comprising:
   i) a milling block comprising:
      a) an upper shell having a front half-face, a back half-face, and an inside attachment surface connecting the half-faces, b) a lower shell having a front half-face, a back half-face, and an inside attachment surface connecting the half-faces, wherein the inside attachment surface of the upper shell is substantially aligned with the inside attachment surface of the lower shell wherein the inside attachment surfaces comprise attachment means, and wherein the attachment means comprise a threaded hole extending from a first inside attachment surface and a mating screw.

26. The device of claim 25 wherein the alignment of the inside attachment surfaces aligns the front half-faces to form a front face in the milling block.

27. The device of claim 26 wherein the alignment of the inside attachment surfaces aligns the back half-faces to form a back face in the milling block.

28. The device of claim 27 wherein the upper shell further comprises a front half-opening formed in the front half-face, the lower shell further comprises a front half-opening formed in the front half-face, and wherein the substantial alignment of the inside attachment surfaces aligns the front half-openings to form a front opening in the milling block.

29. The device of claim 28 wherein the upper shell further comprises a back half-opening formed in the back half-face, the lower shell further comprises a back half-opening formed in the back half-face, and wherein the substantial alignment of the inside attachment surfaces aligns the back half-openings to form a back opening in the milling block.

30. The device of claim 29 wherein the upper shell further comprises an intermediate recess, the lower shell further comprises an intermediate recess, and wherein the substantial alignment of the inside attachment surfaces aligns the intermediate recess to form a housing in the milling block.

31. A vertebral body milling device for creating a contoured disc space between adjacent vertebral bodies of the spine, each of the adjacent vertebral bodies having a vertebral endplate adjacent to the disc space, comprising:

i) a milling block comprising:

a) an upper shell having a front half-face, a back half-face, and an inside attachment surface connecting the half-faces, b) a lower shell having a front half-face, a back half-face, and an inside attachment surface connecting the half-faces, wherein the inside attachment surface of the upper shell is substantially aligned with the inside attachment surface of the lower shell, wherein the inside attachment surfaces comprise alignment means, and wherein the attachment means comprise a hole extending from a first inside attachment surface and a dowel extending from a second inside attachment surface.

* * * * *